US007960578B2

(12) United States Patent
Martinez et al.

(10) Patent No.: US 7,960,578 B2
(45) Date of Patent: Jun. 14, 2011

(54) METHOD FOR THE SYNTHESIS OF PEPTIDES WITHOUT SOLVENT

(75) Inventors: Jean Martinez, Caux (FR); Frédéric Lamaty, Montpellier (FR); Valérie Declerck, Villelongue d'Aude (FR)

(73) Assignees: Centre National de la Recherche Scientifique (CNRS), Paris (FR); Universite de Montpellier I, Montpellier (FR)

( * ) Notice: Subject to any disclaimer, the term of this patent is extended or adjusted under 35 U.S.C. 154(b) by 0 days.

(21) Appl. No.: 12/531,972

(22) PCT Filed: Mar. 21, 2008

(86) PCT No.: PCT/EP2008/053444
§ 371 (c)(1),
(2), (4) Date: Sep. 18, 2009

(87) PCT Pub. No.: WO2008/125418
PCT Pub. Date: Oct. 23, 2008

(65) Prior Publication Data
US 2010/0016631 A1 Jan. 21, 2010

(30) Foreign Application Priority Data
Mar. 21, 2007 (FR) .................................. 07 53970

(51) Int. Cl.
C07C 229/00 (2006.01)
(52) U.S. Cl. ......................................................... 560/41
(58) Field of Classification Search .................. None
See application file for complete search history.

(56) References Cited

U.S. PATENT DOCUMENTS
5,494,897 A * 2/1996 Ishikawa et al. ................. 514/18
2006/0287534 A1 12/2006 Lhermitte et al.

FOREIGN PATENT DOCUMENTS
WO    WO 2005/021517 A1    3/2005

OTHER PUBLICATIONS

Marx, V.; "Watching Peptide Drugs Grow Up," Chem. Eng. News 2005, 83, 17-24.
Kaupp, G.; Schmeyers, J.; Boy, J.; "Quantitative Solid-State Reactions of Amines with Carbonyl Compounds and Isothiocyanates," Tetrahedron 2000, 56, 6899-6911.
Kaupp, G.; Schmeyers, J.; Haak, M.; Marquardt, T.; Herrmann, A. Molecular Crystals and Liquid Crystals Science and Technology, Section A: Molecular Crystals and Liquid Crystals 1996, 276, 315-337.
Kaupp, G.; Naimi-Jamal, M. R.; Stepanenko, V.; "Waste-Free and Facile Solid-State Protection of Diamines, Anthranilic Acid, Diols, and Polyols with Phenylboronic Acid," Chem. Eur. J. 2003, 9, 4156-4160.

Tanaka, K.; Toda, F.; "Solvent-Free Organic Synthesis," Chemical Reviews (Washington, D. C.) 2000, 100, 1025-1074.
Tanaka, K.; Toda, F. Solvent-Free Organic Synthesis, 2003.
Fuller, W. D.; Goodman, M.; Naider, F. R.; Zhu, Y.-F.; "Urethane-Protected α-Amino Acid N-Carboxyanhydrides and Peptide Synthesis," Biopolymers 1996, 40, 183-205.
Audinn, P.; Pothion, G.; Fehrentz, J.-A.; Loffet, A.; Martinez, J.; Paris, J.; "Diastereoselective Synthesis of N-Protected β-Amino-α-hydroxyacides (Norstatines) from Urethane N-Carboxyanhydrides (UNCAs)," J. Chem. Res., Synop. 1999, 282-283.
Chevallet, P.; Fehrentz, J. A.; Kiec-Kononowicz, K.; Devin, C.; Castel, J.; Loffet, A.; Martinez, J.; "Synthesis of chiral N-protected amino acid esters by the use of UNCAs," Lett. Pept. Sci. 1996, 2, 297-300.
Fehrentz, J.-A.; Genu-Dellac, C.; Arnblard, M.; Winternitz, F.; Loffet, A.; Martinez, J.I; "The Use of N-Urethane-protected N-Carboxyanhydrides (UNCAs) in Amino Acid and Peptide Synthesis," Pept. Sci. 1995, I, 124-131.
Fehrentz, J.-A.; Pothiion, C.; Califano, J.-C.; Leffel, A.; Martinez, J.; "Synthesis of Chiral N-Protected α-Amino Aldehydes by Reduction of N-protected N-Carboxyanhydrides (UNCAs)," Tetrahedron Lett. 1994, 35, 9031-9034.
Fehrentz, J. A.; Bourdel, E.; Califano, J. C.; Chaloin, O.; Devin, C.; Garrouste, P.; Lima-Leite, A.-C.; Llinares, M.; Rieunier, F. et al.; "Synthesis of Chiral Urethane N-Alkoxycarbonyl Tetramic Acids from Urethane N-Carboxyanhydrides (UNCAs)," Tetrahedron Lett. 1994, 35, 1557-1560.
Fehrentz, J. A.; Califano, J. C.; Amablard, M.; Loffet, A.; Martinez, J.; "Synthesis of Chiral N-Protected β-Amino Alcohols by the Use of UNCAs," Tetrahedron Lett. 1994, 35, 569-571.
Mc Kiernan, M.; Huck, J.; Fehrentz, J.-A.; Roumestant, M.-L.; Viallefont, P.; Martinez, J.; "Urethane N-Carboxyanhydrides from β-Amino Acids," J. Org. Chem. 2001, 66, 6541-6544.
Paris, M.; Fehrentz, J.-A.; Heitz, A.; Loffet, A.; Martinez, J., "Synthesis of N-protected γ-amino-β-keto-esters from Urethane N-carboxyanhydrides (UNCAs)," Tetrahedron Lett. 1996, 37, 8489-8492.
Paris, M.; Fehrentz, J.-A.; Heitz, A.; Martinez, J.; "Synthesis of N-urethane protected α-alkyl-γ-amino-β-keto-esters from Urethane N-carboxyanhydrides (UNCAs)," Tetrahedron Lett. 1998, 39, 1569-1572.
Paris, M.; Pothion, C.; Michalak, C.; Martinez, J.; Fehrentz, J.-A.; "Synthesis of Cyanoketophosphoranes, Precursors of β-Amino-α-keto-esters from UNCAs.," Tetrahedron Lett. 1998, 39, 6889-6890.
Pothion, C.; Fehrentz, J.-A.; Aumelas, A.; Loffet, A.; Martinez, J.; "Synthesis of Pyrrolidine-2,4-diones from Urethane N-carboxyanhydrides (UNCAs)," Tetrahedron Lett. 1996, 37, 1027-1030.
Pothion, C.; Fehrentz, J. A.; Chevallet, P.; Loffet, A.; Martinez, J.; "Reactivity of UNCAs with Grignard reagents," Lett. Pept. Sci. 1997, 4, 241-244.

(Continued)

Primary Examiner — Daniel M Sullivan
Assistant Examiner — Jennifer C Sawyer
(74) Attorney, Agent, or Firm — Harness, Dickey & Pierce, P.L.C.

(57) ABSTRACT

The disclosure relates to a method for the synthesis of a compound of the formula (I) in which: n is an integer higher than or equal to 1; Rb and each Rn are independently a hydrogen atom, a $C_1$-$C_6$ arylalkyl group or a $C_1$-$C_6$ alkyl group substituted or not by an aryl group, —COOH, $C_1$-$C_6$, —COO-(alkyl), —CONH$_2$, —SH, heteroaryl, —NH$_2$, —NHC(NH)(NH$_2$), $C_1$-$C_6$-s-(alkyl), —OH or phenol; Ra is a N-protective group; Rc is a ORd group in which Rd is a $C_1$-$C_6$ alkyl group or a NReRf group in which Re and Rf Re independently an N-protective group.

18 Claims, No Drawings

OTHER PUBLICATIONS

Tou, J. S.; Vineyard, B. D.; "An N-Carboxyanhydride (NCA) Route to Aspartame," *J. Org. Chem.* 1985, 50, 4982-4986.

Fuller, W.D.; Cohen, M. P.; Shabankareh, M.; Blair, R. K.; Goodman, M.; Naider, F. R.; "Urethane-Protected Amino Acid N-Carboxy Anhydrides and Their Use in Peptide Synthesis," *J. Am. Chem. Soc.* 1990, 112, 7414-7416.

Zhu, Y.-F.; Fuller, W. D.; "Rapid, One-Pot Synthesis of Urethane-Protected Tripeptides," *Tetrahedron Lett.* 1995, 36, 807-810.

Daly, W. H.; Poche, D.; "The Preparation of N-Carboxyanhydrides of α-Amino Acids Using Bis (Trichloromethyl) Carbonate," *Tetrahedron Lett.* 1988, 29, 5859-5862.

Savrda, J.; Chertanova, L.; Wakselman, M.; "Activation of N,N-bis (alkoxycarbonyl) Amino Acids. Synthesis of N-Alkoxycarbbonyl Amino Acid N-Carboxyanhydrides and N,N-Dialkoxycarbonyl Amino Acid Fluorides, and the behavior of these Amino Acid Derivatives." *Tetrahedron* 1994, 50, 5309-5322.

Declerck et al.; "Solvent-free synthesis of peptides," *Angew, Chem. Int. Ed.* 2009, 48, 9318-9321.

McCluskey et al.; "Green chemistry approaches to the Knoevenagel condensation: comparison of ethanol, water and solvent free (dry grind) approaches," Tetrahedron letters, Elsevier, Amsterdam, vol. 43, n° 17, Apr. 22, 2002, pp. 3117-3120, XP004347873.

* cited by examiner

METHOD FOR THE SYNTHESIS OF PEPTIDES WITHOUT SOLVENT

CROSS-REFERENCE TO RELATED APPLICATIONS

This application is a National Phase Entry of International Application No. PCT/EP2008/053444, filed on Mar. 21, 2008, which claims priority to French Application No. 0753970, filed on Mar. 21, 2007, both of which are incorporated by reference herein.

BACKGROUND AND SUMMARY

The present invention relates to a method for the synthesis of peptides without any solvent.

Peptides are presently considered as pharmaceutical active ingredients because of their high therapeutic index and their low toxicity. Because of the development of novel administration systems which increase their bioavailability, it is expected that the market of therapeutic peptides will rapidly develop during future years. But there always exists a need for effective methods for synthesizing these compounds. In spite of well-established production procedures (in solution, in a solid phase, by recombination), there still subsists many development problems associated with the enormous amount of solvent required for the synthesis, notably on solid supports (2,000-5,000 kg for a large peptide).

The field of "green chemistry" is becoming more extensive because of the seriousness of present environmental problems. Several fields of this subject have emerged: the use of an alternative raw material and of a non-toxic reagent, use of natural processes, use of alternative solvents, design of safer chemical products, development of other reaction conditions, minimization of energy consumption . . . . A particular active field lies in the use of alternative solvents such as aqueous, ionic, fluorinated or supercritical liquids, in order to replace volatile organic or chlorinated solvents and in order to solve the problems of treating or recycling solvent-based waste.

An alternative approach consists of producing chemical reactions in the absence of a solvent. Techniques such as mixing or milling of solids have proved to be efficient. Nevertheless, no application of these techniques to fields such as peptide or amino acid synthesis has been undertaken, in spite of the importance of these biomolecules.

The authors of the present invention have discovered surprisingly novel routes for synthesizing peptides under conditions without any solvent. Surprisingly, the authors have achieved the coupling of carboxy anhydrides of amino acids protected by a urethane (Urethane-protected N-CarboxyAnhydride (UNCA)), with amino acids or amino esters, while all these compounds remained in their solid form, under conditions of ball milling and at room temperature.

More specifically, the invention relates to a method for synthesizing a compound of the following formula (I)

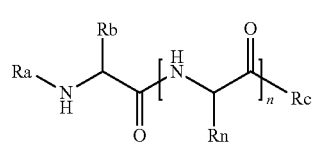

wherein:

n is an integer larger than or equal to 1, advantageously comprised between 1 and 100, more advantageously comprised between 1 and 50, still more advantageously equal to 1 or 2;

Rb and each Rn represent independently of each other a hydrogen atom, an aryl ($C_1$-$C_6$ alkyl) group, or a $C_1$-$C_6$ alkyl group either substituted or not by an aryl group, —COOH, —COO—($C_1$-$C_6$ alkyl), —CONH$_2$, —SH, heteroaryl, —NH$_2$, —NHC(NH)(NH$_2$), —S—($C_1$-$C_6$ alkyl)-OH or phenol group, the groups of which —COOH, —NH$_2$, OH, SH and NH are optionally protected with one or more identical or different N-protective or O-protective groups and different from Ra, advantageously these N-protective and/or O-protective group(s) are stable under conditions for removing the Ra group;

Ra represents an N-protective group;

Rc represents an —ORd group wherein Rd represents a $C_1$-$C_6$ alkyl group or an —NReRf group wherein Re and Rf represent independently of each other an N-protective group, characterized in that it comprises a step (a) consisting of reacting in the presence of a base and without any solvent, the compound of the following formula (II):

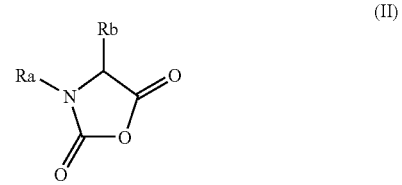

wherein Ra and Rb are as defined earlier, with the compound of the following formula (III):

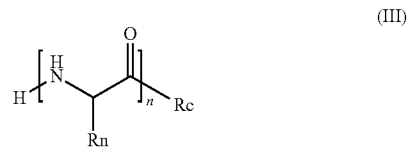

wherein n, Rn and Rc are as defined earlier, as well as its pharmaceutically acceptable salts, preferably chlorides, acetates and trifluoroacetates.

In the sense of the present invention, by the term "without any solvent" is meant that the reaction occurs in the absence of a solvent. A solvent according to the invention is a product which solubilizes the reagents but does not directly participate in the reaction. Thus, within the scope of the present invention, the base is not a solvent.

Moreover, in the method according to the invention, all the reagents used are in the solid state. This is in particular the case of the compounds of formula II and III and of the base. Thus, this reaction occurs in the solid state and not in solution. Advantageously, these reagents are in a finely divided solid form, as obtained by ball-milling. The advantage of this type of reaction is to suppress the use of a solvent (green chemistry) but also to facilitate application of the reaction, treatment and to allow very pure products to be obtained.

By the term of "$C_1$-$C_6$ alkyl group" is meant in the sense of the present invention any linear or branched alkyl group with 1-6 carbon atoms, in particular the methyl, ethyl, n-propyl, isopropyl, n-butyl, iso-butyl, sec-butyl, t-butyl, n-pentyl, n-hexyl groups. Advantageously this is a methyl or t-butyl group. By the term of "aryl group" is meant in the sense of the present invention one or more aromatic rings having 5-8 carbon atoms, which may be placed side by side or fused. In particular, aryl groups may be monocyclic or bicyclic groups, preferably a phenyl, napthyl, tetrahydronaphthyl or indanyl group. Advantageously, this is a phenyl group.

By the term of "heteroaryl group", is meant in the sense of the present invention any hydrocarbon aromatic group with 3-9 atoms, containing one or two heteroatoms, such as for example sulfur, nitrogen or oxygen atoms. The heteroaryl group according to the present invention may be formed with one or two fused cycles or cycles placed side by side. Examples of heteroaryl groups are the furyl, isoxazyl, pyridyl, pyrimidyl, benzimidazole, benzoxazole, benzothiazole groups.

By the term of "N-protective group" is meant in the sense of the present invention any substituent which protects the $NH_2$ group against undesirable reactions such as the N-protective groups described in Greene, "Protective Groups In Organic Synthesis", (John Wiley & Sons, New York (1981)) and Harrison et al. "Compendium of Synthetic Organic Methods", Vols. 1-8 (J. Wiley & Sons, 1971-1996). The N-protective groups comprise carbamates, amides, N-alkylated derivatives, amino acetal derivatives, N-benzylated derivatives, imine derivatives, enamine derivatives and N-heteroatom derivatives. In particular, the N-protective group comprises the formyl, acetyl, benzoyl, pivaloyl, phenylsulfonyl, benzyl (Bn), t-butyloxycarbonyl (boc), benzyloxycarbonyl (cbz), p-methoxybenzyloxycarbonyl, p-nitrobenzyl-oxycarbonyl, trichloroethoxycarbonyl (troc), allyloxycarbonyl (alloc), 9-fluorenylmethyloxycarbonyl (fmoc), trifluoroacetyl group, benzyl carbamates (either substituted or not) and the like. Either boc or cbz as a N-protective group is advantageous to use because of the relative facility of removal, for example with moderate acids in the case of boc, for example trifluoroacetic acid, or hydrochloric acid in ethyl acetate; or by catalytic hydrogenation in the case of cbz. Advantageously, this is the boc group.

By the term of "O-protective group" is meant in the sense of the present invention any substituent which protects the hydroxyl or carboxyl group, i.e. a reactive oxygen atom, against undesirable reactions, such as the O-protective groups described in Greene, "Protective Groups In Organic Synthesis", (John Wiley & Sons, New York (1981)) and Harrison et al. "Compendium of Synthetic Organic Methods", Vols. 1-8 (J. Wiley & Sons, 1971-1996). The O-protective groups comprise methyl or alkyl ethers either substituted or not, for example methoxymethyl, benzyloxymethyl, 2-methoxyethoxymethyl, 2-(trimethylsilyl)ethoxymethyl, t-butyl, benzyl and triphenylmethyl, benzyl ethers (either substituted or not), tetrahydropyranyl ethers, allyl ethers, substituted ethyl, for example 2,2,2-trichloroethyl, ethers, silyl ethers or alkylsilyl ethers, for example trimethylsilyl, t-butyl dimethyl silyl, and t-butyldiphenyl silyl, heterocyclic ethers; and esters prepared by reaction of the hydroxyl group with a carboxylic acid, for example tert-butyl, benzyl, or methyl esters, carbonates in particular benzyl carbonate or haloalkyl carbonate, acetate, propionate, benzoate and the like. Advantageously this is the benzyl group.

Subsequently, the compounds of formula I may be deprotected so as to obtain the peptides for which the —OH, —$NH_2$, —SH, —NH and —COOH functions are non-protected.

In an advantageous embodiment of the invention, n is equal to 1 and step (a) consists of reacting in the presence of a base and without any solvent the compound of formula (II) with the compound of the following formula (III-1):

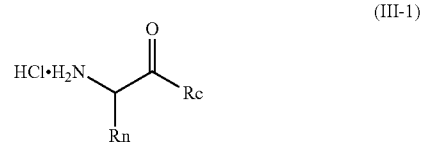

(III-1)

wherein R1 and Rc are as defined earlier so as to obtain the compound of the following formula (I-1):

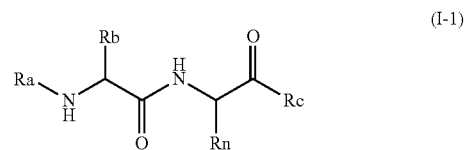

(I-1)

wherein Ra, Rb, Rc and Rn are as defined earlier.

Step (a) is advantageously carried out by means of ball-milling. It is particularly advantageous to carry out the step (a) from freshly prepared starting products of formula (II) and (III). The base is a solid base and may advantageously be selected from the group formed by carbonates, in particular sodium, potassium and cesium hydrogencarbonates, and sodium, potassium and cesium carbonates. Advantageously this is sodium hydrogencarbonate.

The substituents Rb and each substituent Rn may independently be selected from the group consisting of hydrogen, —$CH_3$, the benzyl group, —$CH_2CONH_2$, —$CHCH_3C_2H_5$, —$(CH_2)_3NHC(NH)(NH_2)$, —$CH(OH)CH_3$, —$CH_2COOH$, —$CH_2SH$, —$CH_2CH_2COOH$, —CH2CH2CONH2, imidazolyl methyl, propyl, —CH2CH(CH3)2, —(CH2)4NH2, —$(CH_2)_2SCH_3$, —$CH_2OH$, indol-2-ylmethyl, p-methylphenol, isopropyl groups. As indicated earlier, the $NH_2$, NH, COOH, SH and OH function of these groups are advantageously protected by one or more identical or different, O-protective and/or N-protective groups and different from Ra. Advantageously, these N-protective and/or O-protective group(s) are stable under the conditions for removing the Ra group.

In an advantageous embodiment of the invention:

Ra, Re and Rf are selected independently of each other from the group consisting of tert-butyloxy carbonyl, 9-fluorenylmethyloxycarbonyl, benzyloxycarbonyl, nitro-veratryloxy carbonyl and/or Rb is selected from the group consisting of isopropyl, benzyl and —$CH_2COOt$-Bu and/or each Rn is selected independently of the others from the group consisting of methyl, benzyl and —$CH_2CH(CH_3)_2$ and/or Rd is selected from the group consisting of methyl and tertiobutyl.

In an advantageous embodiment of the invention, the compound (II) is selected from the group consisting of the compounds of the following formulae (II-a), (II-b) and (II-c):

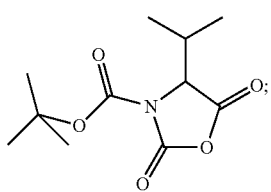
(II-a)

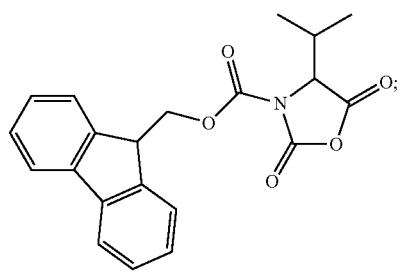
(II-b)

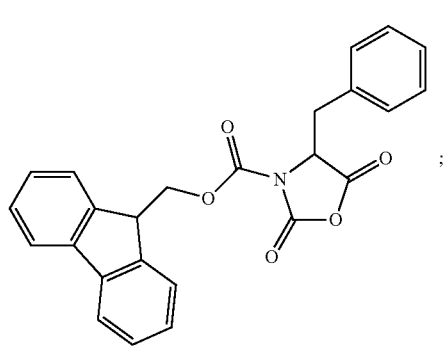
(II-c)

the compound (III) is selected from the group consisting of the compounds of the following formulae (III-a), (III-b), (III-c), (III-d) and (III-e):

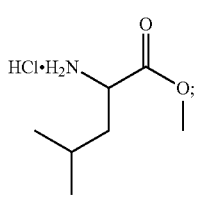
(III-a)

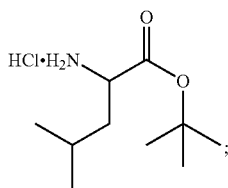
(III-b)

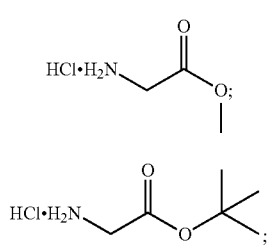
(III-c)

(III-d)

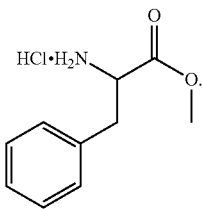
(III-e)

In another advantageous embodiment of the invention, the compound of formula (II) has the following formula (II-2):

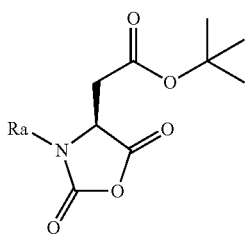
(II-2)

wherein Ra is as defined earlier, the compound of formula (III) has the following formula (III-2):

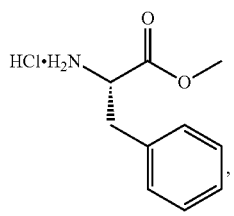
(III-2)

and the compound of formula (I) has the following formula (I-2):

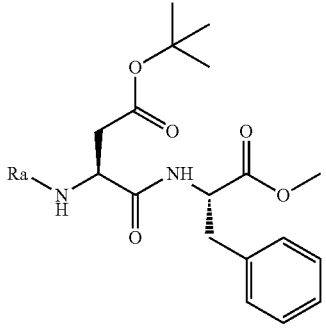
(I-2)

wherein Ra is as defined earlier.

The compound of formula (II-2) may be prepared by a method comprising the following successive steps:

1) protecting the amine group of the compound of the following formula (IV):

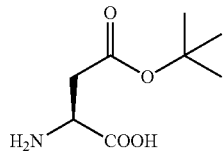

(IV)

with an N-protective group Ra in order to form the compound of the following formula (V):

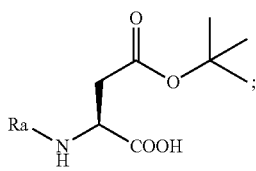

(V)

2) reacting the compound of formula (V) with a benzyl halide in the presence of a base, advantageously cesium carbonate, in order to obtain the compound of the following formula (VI):

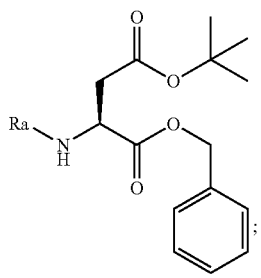

(VI)

wherein Ra is as defined above;

3) protecting the amine group of the compound of formula (VI) with an N-protective group Rg in order to form the compound of the following formula (VII):

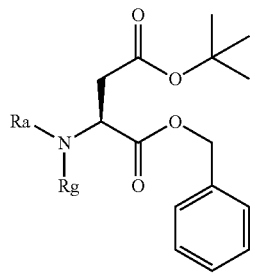

(VII)

wherein Ra and Rg are as defined above;

4) reducing the compound of formula (VII) into a compound of the following formula (VIII):

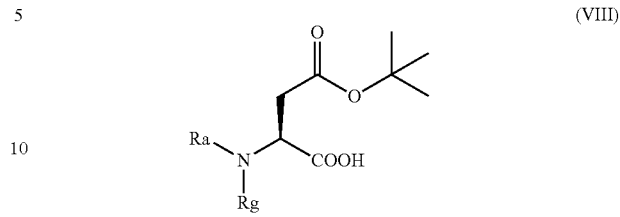

(VIII)

wherein Ra and Rg are as defined above;

5) cyclizing the compound of formula (VIII) into a compound of formula (II-2) by reaction with DMF and oxalyl chloride. The substituents Ra and Rg advantageously represent tert-butyloxycarbonyl.

In an advantageous embodiment, the method comprises the following additional successive steps:

(b) reacting the compound of formula (I-2) obtained in step (a) with an acid, advantageously hydrochloric acid gas, in order to form the compound of the following formula (I-3):

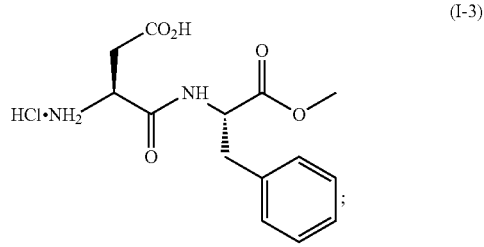

(I-3)

(c) reacting the compound of formula (I-3) with a base, advantageously sodium bicarbonate, in order to form the compound of the following formula (I-4):

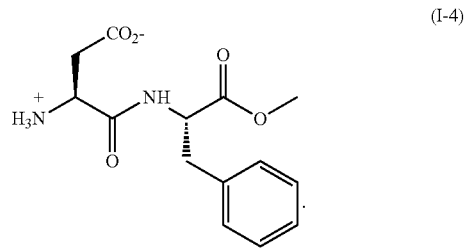

(I-4)

DETAILED DESCRIPTION

The invention will now be illustrated in a non-limiting way by the following examples.

Example 1

Synthesis of Dipeptides

The inventors have conducted the reaction without any solvent between a UNCA and an amino acid derivative in order to form a dipeptide according to the equation below:

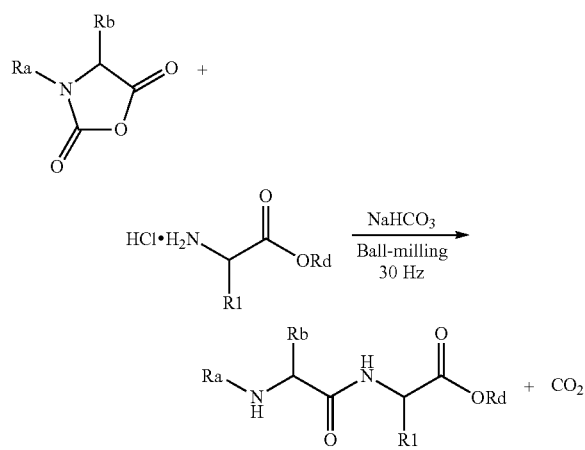

This reaction was tested in the Boc-Val-NCA, Fmoc-Val-NCA and Boc-Phe-NCA (1 eq.) coupling with various amino acids (1 eq.) in the presence of NaHCO$_3$ (1.5 eq.) in a quenched steel tank containing steel balls. The tank was stirred for 1 hour at a frequency of 30 Hz. The analysis of the reaction medium detected the exclusive existence of the dipeptide. The results are reported in Table 1 with various UNCAs and amino acid derivatives.

TABLE 1

| UNCA | Amino acids | Dipeptides | Conversion (%) | Yield (%) |
|---|---|---|---|---|
| Boc-Val-NCA | HCl•H-Leu-OMe | Boc-Val-Leu-OMe | 100 | 87 |
| | HCl•H-Leu-OBut | Boc-Val-Leu-OBut | 97 | 85 |
| | HCl•H-Ala-OMe | Boc-Val-Ala-OMe | 100 | 100 |
| | HCl•H-Ala-OBut | Boc-Val-Ala-OBut | 100 | 100 |
| | HCl•H-Phe-OMe | Boc-Val-Phe-OMe | 100 | 88 |
| Fmoc-Val-NCA | HCl•H-Leu-OMe | Fmoc-Val-Leu-OMe | 90 | — |
| | HCl•H-Leu-OBut | Fmoc-Val-Leu-OBut | 92 | — |
| | HCl•H-Ala-OMe | Fmoc-Val-Ala-OMe | 100 | 76 |
| | HCl•H-Ala-OBut | Fmoc-Val-Ala-OBut | 78 | — |
| | HCl•H-Phe-OMe | Fmoc-Val-Phe-OMe | 93 | — |
| Boc-Phe-NCA | HCl•H-Leu-OMe | Boc-Phe-Leu-OMe | 85 | — |
| | HCl•H-Leu-OBut | Boc-Phe-Leu-OBut | 100 | 70 |
| | HCl•H-Ala-OMe | Boc-Phe-Ala-OMe | 99 | 79 |
| | HCl•H-Ala-OBut | Boc-Phe-Ala-OBut | 100 | 73 |
| | HCl•H-Phe-OMe | Boc-Phe-Phe-OMe | 58 | — |

The various UNCA derivatives do not have the same reactivity profile. In all the cases, Boc-Val-NCA was quantitatively transformed with view to forming the dipeptide while Fmoc-Val-NCA in both cases gave a slightly smaller yield.

It should be noted that the best examples were obtained with a freshly prepared starting substance, either UNCA or the amino ester. The reaction was otherwise incomplete and hydrolysis of UNCA was observed.

Example 2

Synthesis of Aspartame

Aspartame, or α-L-aspartyl-L-phenylalanine-methyl ester, is a nutritive sweetener approximately 150 times more intense than saccharose. This is a commercially attractive dipeptide which however has not yet been prepared via UNCAs, neither in the presence nor in the absence of solvent.

The inventors obtained the protected aspartame in a step from H-Phe-OMe.HCl (III-e) and from Boc-Asp(O-t-Bu)—NCA (II-a) by ball-milling without any solvent.

The protective groups Boc and t-Bu were selected since they may be cleaved at the same time under acid conditions. In order to further avoid the use of any solvent, HCl gas was used for removing the protective groups.

2.1. Preparation of Boc-Asp(O-tBu)—NCA (II-a)

This method consisted in the cyclization of the free carboxylic acid with a main chain with one of the Bocs protecting the amine function, therefore first of all requiring the preparation of (Boc)$_2$-Asp(O-t-Bu)—OH (VII-a). This was achieved by esterification of the α-carboxylic acid of Boc-Asp(O-t-Bu)—OH (V-a) into the benzyl ester (VI(a)), followed by a reaction with Boc$_2$O in the presence of DMAP in order to give the amino compound protected by two Boc groups (VII-a), and then by deprotection of the benzyl ester group by hydrogenation in order to give (VIII-a).

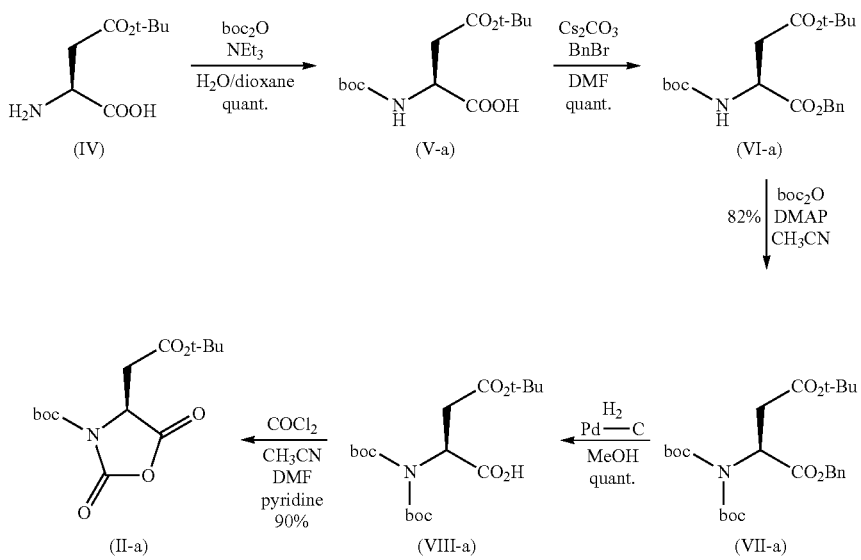

The following step consisted in the cyclization of the amino acid (VIII-a) protected with Vilsmeier's salt. The best results were obtained by forming the salt of DMF and oxalyl chloride in acetonitrile. The compound (II-a) was obtained with 90% yield.

2.2. Preparation of the Aspartame

The procedure described above for preparing dipeptides was applied to the preparation of aspartame.

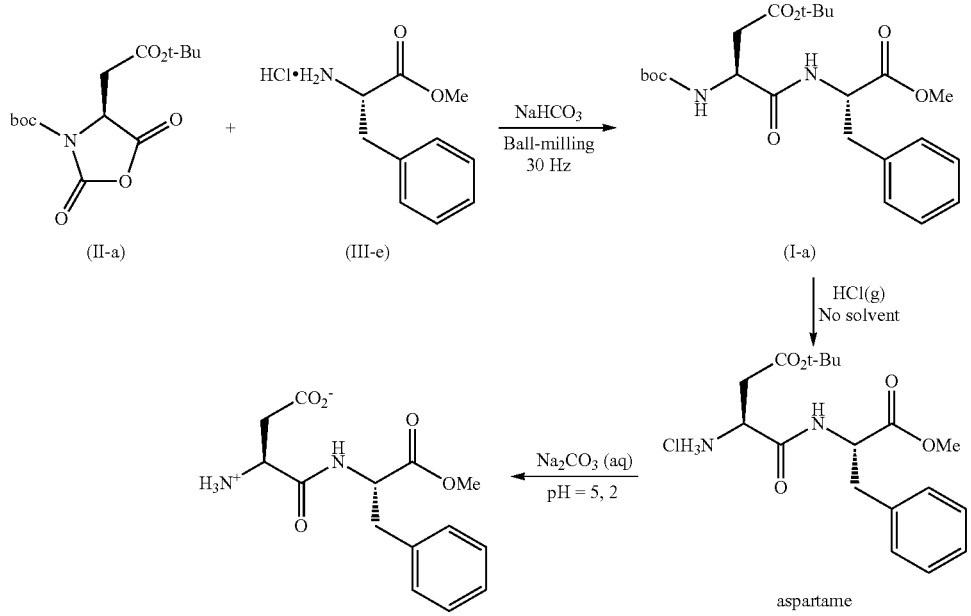

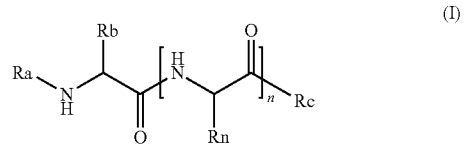

Starting with Boc-Asp(O-t-Bu)—NCA (II-a) and with H-Phe-OMe.HCl (III-e), the dipeptide (I-a) was obtained after 1 hour of ball-milling.

Next, it reacted directly with HCl gas for 2 hours in the absence of any solvent in order to remove the protective groups Boc and t-Bu and for obtaining the hydrochloride form of aspartame. Let us note that the removal of the protective groups Boc and t-Bu only gave volatile secondary products. It should also be noted that the yield of both steps was quantitative.

The hydrochloride was dissolved in water and the pH was adjusted to 5.2 with an aqueous solution of $Na_2CO_3$. The obtained aspartame precipitated. It was filtered and dried in vacuo in order to obtain a solid with 40% yield.

The aspartame was therefore obtained in pure form, without using any organic solvents and without any organic secondary products. The single purification step consisted in precipitation from water in order to obtain solid aspartame.

The invention claimed is:

1. A method for synthesizing a compound of the following formula (I)

(I)

wherein:
n is an integer larger than or equal to 1;
Rb and each Rn represent independently of each other a hydrogen atom, an aryl ($C_1$-$C_6$ alkyl) group, or a $C_1$-$C_6$ alkyl group either substituted or not by an aryl group, —COOH, —COO—($C_1$-$C_6$ alkyl), —CONH$_2$, —SH, heteroaryl, —NH$_2$, —NHC(NH)(NH$_2$), —S—($C_1$-$C_6$ alkyl), —OH or phenol;

Ra represents an N-protective group;

Rc represents an —ORd group wherein Rd represents a $C_1$-$C_6$ alkyl group or an —NReRf group wherein Re and Rf represent independently of each other an N-protective group, wherein it comprises a step (a) consisting of milling in the presence of a base and without any solvent, the compound of the following formula (II):

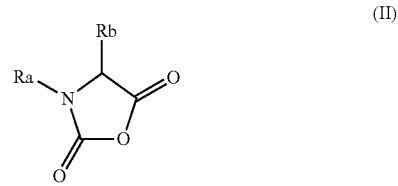

wherein Ra and Rb are as defined earlier, with the compound of the following formula (III):

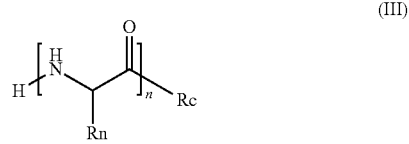

wherein n, Rn and Rc are as defined earlier, as well as its pharmaceutically acceptable salts.

2. The method according to claim 1, wherein n is equal to 1 and in that step (a) consists of reacting in the presence of a base and without any solvent the compound of formula (II) with the compound of the following formula (III-1):

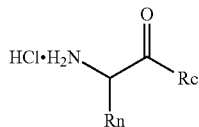
(III-1)

wherein R1 and Rc are as defined earlier so as to obtain the compound of the following formula (I-1):

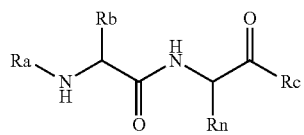
(I-1)

wherein Ra, Rb, Rc and Rn are as defined earlier.

3. The method according to claim 1, wherein step (a) is carried out by means of ball-milling.

4. The method according to claim 1, wherein the base is selected from the group consisting of carbonates.

5. The method according to claim 1, wherein Rb and each Rn are independently selected from the group consisting of hydrogen, —CH$_3$, the benzyl group, —CH$_2$CONH$_2$, —CHCH$_3$C$_2$H$_5$, —(CH$_2$)$_3$NHC(NH)(NH$_2$), —CH(OH)CH$_3$, —CH$_2$COOH, —CH$_2$SH, —CH$_2$CH$_2$COOH, —CH$_2$CH$_2$CONH$_2$, imidazolylmethyl, propyl, —CH$_2$CH(CH$_3$)$_2$, —(CH$_2$)$_4$NH$_2$, —(CH$_2$)$_2$SCH$_3$, —CH$_2$OH, indol-2-ylmethyl, p-methylphenol, isopropyl groups.

6. The method according to claim 1, wherein

Ra, Re and Rf are selected independently of each other from the group consisting of tert-butyloxycarbonyl, 9-fluorenylmethyloxycarbonyl, benzyloxycarbonyl, nitro-veratryloxycarbonyl, Rb is selected from the group consisting of isopropyl, benzyl and —CH$_2$COOt-Bu;

each Rn is selected independently of the others from the group consisting of methyl, benzyl and —CH$_2$CH(CH$_3$)$_2$;

Rd is selected from the group consisting of methyl and tertiobutyl.

7. The method according to claim 2, wherein:

the compound (II) is selected from the group consisting of the compounds of the following formulae (II-a), (II-b) and (IIc):

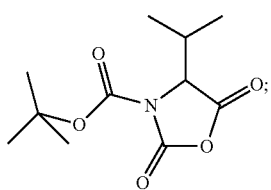
(II-a)

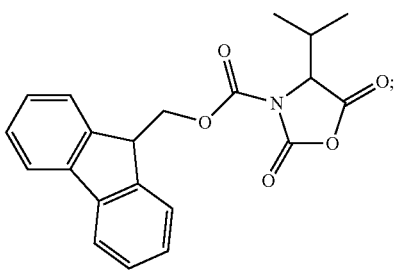
(II-b)

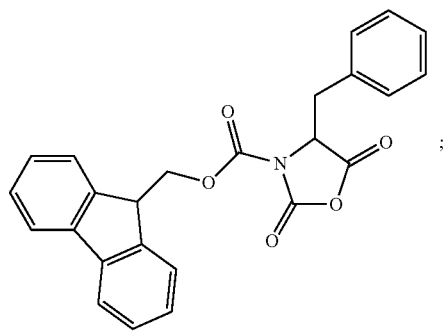
(II-c)

the compound (III) is selected from the group consisting of the compounds of the following formulae (III-a), (III-b), (III-c), (III-d) and (III-e):

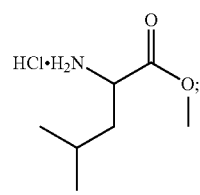
(III-a)

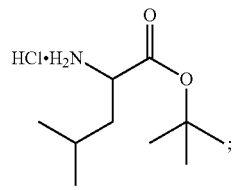
(III-b)

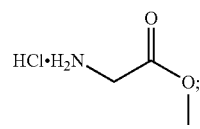
(III-c)

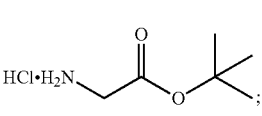
(III-d)

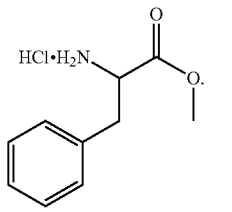
(III-e)

8. The method according to claim 2, wherein:
the compound of formula (II) has the following formula (II-2):

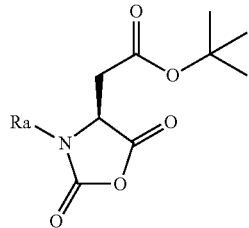
(II-2)

wherein Ra is as defined in claim 1,
the compound of formula (III) has the following formula (III-2):

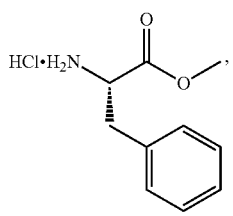
(III-2)

and the compound of formula (I) has the following formula (I-2):

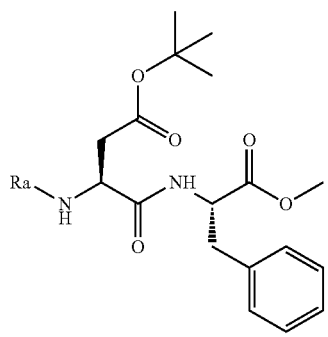
(I-2)

wherein Ra is as defined in claim 1.

9. The method according to claim 8, wherein the compound of formula (II-2) is prepared by a method comprising the following successive steps:
(a) protecting the amine group of the compound of the following formula (IV):

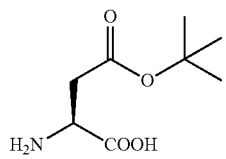
(IV)

with an N-protective group Ra in order to form the compound of the following formula (V):

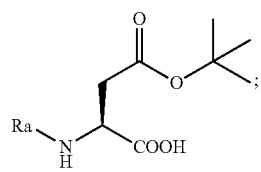
(V)

(b) reacting the compound of formula (V) with a benzyl halide in the presence of a base in order to obtain the compound of the following formula (VI):

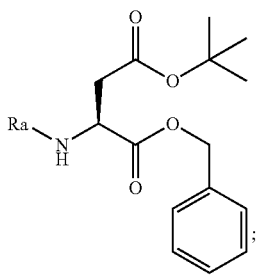
(VI)

wherein Ra is as defined above;
(c) protecting the amine group of the compound of formula (VI) with an N-protective group Rg in order to form the compound of the following formula (VII):

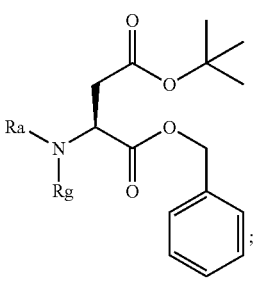
(VII)

wherein Ra and Rg are as defined above;
(d) reducing the compound of formula (VII) into a compound of the following formula (VIII):

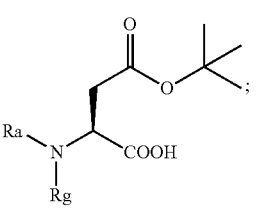
(VIII)

wherein Ra and Rg are as defined above; and (e) cyclizing the compound of formula (VIII) into a compound of formula (II-2) by reaction with DMF and oxalyl chloride.

10. The method according to claim 9, wherein Ra and Rg represent tert-butyloxycarbonyl.

11. The method according to claim 8, wherein it comprises the following additional successive steps:

(b) reacting the compound of formula (I-2) obtained in step (a) with an acid in order to form the compound of the following formula (I-3):

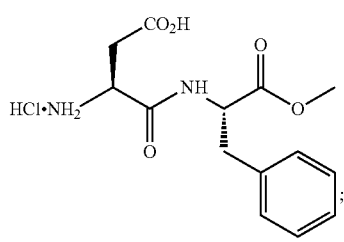
(I-3)

(c) reacting the compound of formula (I-3) with a base in order to form the compound of the following formula (I-4):

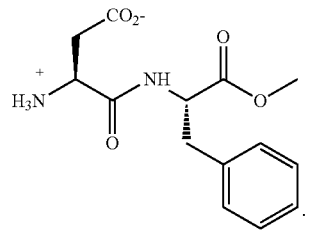
(I-4)

12. The method according to claim 1, wherein the functions $NH_2$, NH, COOH, OH, SH of the Rb and Rn groups are protected by one or more identical or different N-protective or O-protective groups and different from the Ra.

13. The method according to claim 1, wherein n is comprised between 1 and 100.

14. The method according to claim 13, wherein n is comprised between 1 and 50.

15. The method according to claim 14, wherein n=1 or 2.

16. The method according to claim 1, wherein the pharmaceutically acceptable salts are chosen in the group consisting of chlorides, acetates and trifluoroacetates.

17. The method according to claim 4, wherein the carbonates are chosen from the group consisting of sodium, potassium and cesium hydrogencarbonates, and sodium, potassium and cesium carbonates.

18. The method according to claim 5, wherein the functions $NH_2$, NH, COOH, OH, SH of the Rb and Rn groups are protected by one or more identical or different N-protective or O-protective groups and different from the Ra.

* * * * *